(12) United States Patent
Su et al.

(10) Patent No.: US 11,209,414 B2
(45) Date of Patent: Dec. 28, 2021

(54) METHOD FOR DETERMINING QUALITY LEVEL OF IRON AND STEEL PRODUCT

(71) Applicants: Central Iron and Steel Research Institute, Beijing (CN); BEIJING MATDAO TECHNOLOGY CO., LTD., Beijing (CN)

(72) Inventors: Hang Su, Beijing (CN); Tao Pan, Beijing (CN); Xiaoling Chen, Beijing (CN); Caifu Yang, Beijing (CN); Feng Chai, Beijing (CN); Qingyou Liu, Beijing (CN)

(73) Assignees: Central Iron and Steel Research Institute, Beijing (CN); BEIJING MATDAO TECHNOLOGY CO., LTD., Beijing (CN)

( * ) Notice: Subject to any disclaimer, the term of this patent is extended or adjusted under 35 U.S.C. 154(b) by 462 days.

(21) Appl. No.: 16/164,972

(22) Filed: Oct. 19, 2018

(65) Prior Publication Data
US 2019/0137471 A1 May 9, 2019

(30) Foreign Application Priority Data
Nov. 3, 2017 (CN) .......................... 201711072398.X

(51) Int. Cl.
G01N 33/20 (2019.01)
G06F 17/18 (2006.01)

(52) U.S. Cl.
CPC ............ G01N 33/20 (2013.01); G06F 17/18 (2013.01)

(58) Field of Classification Search
CPC ................................ G01N 33/20; G06F 17/18
See application file for complete search history.

(56) References Cited

U.S. PATENT DOCUMENTS

| 5,974,246 | A | | 10/1999 | Nakazawa | |
|---|---|---|---|---|---|
| 6,085,183 | A | * | 7/2000 | Horn | G05B 13/0285 706/45 |
| 2006/0009864 | A1 | * | 1/2006 | Kranner | G05B 23/0248 700/28 |
| 2006/0108721 | A1 | * | 5/2006 | Weaver | C21B 7/14 266/90 |
| 2006/0282186 | A1 | * | 12/2006 | Hansen | G05B 13/024 700/97 |

FOREIGN PATENT DOCUMENTS

| CN | 102090705 A | 6/2011 |
|---|---|---|
| CN | 104376424 A | 2/2015 |
| CN | 104573278 A | 4/2015 |
| CN | 104751288 A | 7/2015 |
| CN | 104850926 A | 8/2015 |
| CN | 105486831 A | 4/2016 |
| DE | 10261124 A1 | 7/2004 |

* cited by examiner

Primary Examiner — Walter L Lindsay, Jr.
Assistant Examiner — Geoffrey T Evans
(74) Attorney, Agent, or Firm — Novick, Kim & Lee, PLLC; Sang Ho Lee; Hyun Woo Shin

(57) ABSTRACT

Provided is a method for determining a quality level of an iron and steel product. The method includes: obtaining a plurality of first parameters related to a quality of an iron and steel product; fusing the plurality of first parameters to obtain a comprehensive quality evaluation parameter; and determining a quality level of the iron and steel product based on the comprehensive quality evaluation parameter.

13 Claims, 5 Drawing Sheets

METHOD FOR DETERMINING QUALITY LEVEL OF IRON AND STEEL PRODUCT

CROSS-REFERENCE TO RELATED APPLICATION

This application claims the priority under 35 U.S.C. § 119 of Chinese Patent Application No. 201711072398.X, filed on Nov. 3, 2017, the entire disclosure of which is incorporated herein by reference for all purposes.

TECHNICAL FIELD

The present disclosure relates to the field of iron and steel materials, particularly, to a method for determining quality level of an iron and steel product.

BACKGROUND ART

Conventional product test and certification, e.g., Chinese Classification Society (CCS) certification, are a two-value system of the "threshold" level, that is, the finally provided test and evaluation results are "Qualified" or "Unqualified", and a producer only needs to satisfy "conform to the requirement of the specified standards". Under the conditions of intensifying market competition, in order to improve the rate of winning a bid, costs and price are lowered even by means of various unorthodox means, thereby initiating a wide "low cost and low quality" market competitive state in iron and steel industry, which causes a negative impact on the iron and steel industry and its reputation. For example, some steel makers of ship-hull plates like to reduce the content of alloying elements of products by a large margin through an extreme "ultra fine grain" technology, aiming to reduce costs of materials in the shipbuilding industry. As a result, a substantial reduction of strength and toughness of welded joints due to lack of alloying elements and according grain coarsening during welding causes troubles in the field fabrication of steel plates at shipyards. In another case concerning stainless steel, the contents of precious alloy elements, such as Cr, Ni, Mo, are often controlled near a lower limit area by its standard by steel provider in order to cut down the cost despite the service performance. While the design of a user for corrosion resisting life of the materials are generally based on medium limit components specified by the standard. The mismatch between production control and design ideas usually results in premature failure of important equipments and parts of the user. Therefore, users of the industry are lack of confidence in long-term quality stability and service security of key materials, which has become a critical obstacle to innovative development of iron and steel producers and technical progress of a manufacturing industry.

Therefore, based on the above reasons, a new numerical evaluation technology for determining a quality level of an iron and steel product is required to overcome disadvantages of the current two-value test and evaluation method of the "threshold" form and make up for deficiencies in the prior art.

SUMMARY

The present disclosure provides a method and equipment for evaluating and determining a quality level of an iron and steel product.

According to one aspect of the present disclosure, a method for determining a quality level of an iron and steel product may include: obtaining a plurality of first parameters related to a quality of an iron and steel product; fusing the plurality of first parameters to obtain a comprehensive quality evaluation parameter; and determining a quality level of the iron and steel product based on the comprehensive quality evaluation parameter.

According to exemplary embodiments of the present disclosure, each first parameter may be obtained through corresponding at least one second parameter, wherein when a first parameter may be obtained through corresponding a plurality of second parameters, it may be obtained by fusing corresponding the plurality of second parameters.

According to exemplary embodiments of the present disclosure, a plurality of first parameters may include some intrinsic parameters which exhibit its own property of the iron and steel product and an epitaxial parameters which reflects impact on the quality of the iron and steel product.

According to exemplary embodiments of the present disclosure, the epitaxial parameters may be parameters representing research and development capability of a manufacturer of the iron and steel product and/or technical capabilities of respective technological processes during a productive process of the iron and steel product.

According to exemplary embodiments of the present disclosure, the intrinsic parameters may be parameters which directly exhibit its own property of the iron and steel product and a parameter which indirectly exhibit its own property of the iron and steel product.

According to exemplary embodiments of the present disclosure, at least one second parameter corresponding to the epitaxial parameter may include at least one parameter of technical capability parameter of production line equipment, technical capability parameter of quality testing, and technical capability parameter of research and development.

According to exemplary embodiments of the present disclosure, the technical capability parameter of production line equipment may be a parameter reflecting the technical capability of production line equipment and obtained through data associated with production equipments and production process parameters of iron and steel products corresponding to respective technological processes during a productive process for producing the iron and steel product. The technical capability parameter of quality testing may be a parameter reflecting the technical capability of quality testing and obtained through data associated with testing machines and technical capabilities of iron and steel products during a quality testing process for producing the iron and steel product. The technical capability parameter of research and development may be a parameter reflecting the enterprise technical capability of research and development and obtained through data associated with research and development capabilities of iron and steel producers.

According to exemplary embodiments of the present disclosure, at least one second parameter corresponding to the epitaxial parameter may include a first-type second parameter and/or a second-type second parameter, wherein the first-type second parameter may be obtained by fusing corresponding a plurality of third parameters, and the second-type second parameter may be obtained through the following steps: obtaining evaluation processing data among multiple types of data corresponding to the second-type second parameter by evaluating each type of data using an evaluation function, and then obtaining the corresponding second parameter by fusing all evaluation processing data.

According to exemplary embodiments of the present disclosure, a plurality of second parameters corresponding to the intrinsic parameter may include at least one parameter of a product batch statistical parameter, a product quality testing parameter, a product supply parameter and a product certification parameter.

According to exemplary embodiments of the present disclosure, the product batch statistical parameter may be a parameter reflecting quality stability and an average level of the iron and steel product and obtained based on batch statistical data of the iron and steel product produced by the production line of the iron and steel product over a period of time. The product quality testing parameter may be a parameter reflecting the quality of the iron and steel product and obtained based on property testing data of the iron and steel product. The product supply parameter may be a parameter obtained based on data associated with supply achievements of the iron and steel product. And the product certification parameter may be a parameter obtained based on third party certification data of the iron and steel product.

According to exemplary embodiments of the present disclosure, at least one second parameter corresponding to the intrinsic parameter may include a first-type second parameter and/or a second-type second parameter, wherein the first-type second parameter may be obtained by fusing corresponding a plurality of third parameters, and the second-type second parameter may be obtained through the following steps: obtaining evaluation processing data among multiple types of data corresponding to the second-type second parameter by evaluating the each type of data using an evaluation function; and obtaining the corresponding second parameter by fusing all evaluation processing data.

According to exemplary embodiments of the present disclosure, the first-type second parameter in the at least one second parameter corresponding to the epitaxial parameter may include the technical capability parameter of production line equipment.

According to exemplary embodiments of the present disclosure, any one third parameter among a plurality of third parameters corresponding to the technical capability parameter of production line equipment may be obtained through the following steps: calculating evaluation processing data corresponding to each type of data among multiple types of data corresponding to the any one third parameter using an evaluation function and the each type of data; and fusing all evaluation processing data corresponding to the multiple types of data corresponding to the any one third parameter to obtain the any one third parameter. The any third parameter may be a parameter reflecting the technical capability of one production line corresponding to one process segment among a plurality of process segments during the process of producing the iron and steel product. Multiple types of data corresponding to the any one third parameter may include data associated with equipments and process parameters of the one production line.

According to exemplary embodiments of the present disclosure, the plurality of third parameters corresponding to the technical capability parameter of production line equipment may include at least two parameters of a melting-casting production line parameter, a thermoforming production line parameter, a heat treatment production line parameter and a working production line parameter. The melting-casting production line parameter may be a parameter reflecting the technical capability of a melting-casting production line corresponding to a melting-casting procedure segment. The thermoforming production line parameter may be a parameter reflecting the technical capability of a thermoforming production line corresponding to a thermoforming procedure segment. The heat treatment production line parameter is a parameter reflecting the technical capability of a heat treatment production line corresponding to a heat treatment procedure segment. The working production line parameter may be a parameter reflecting the technical capability of a working production line corresponding to a working procedure segment.

According to exemplary embodiments of the present disclosure, the obtaining the technical capability parameter of production line equipment by fusing corresponding the plurality of third parameters may include: fusing corresponding the plurality of third parameters using a procedure succession (production line succession) relation. When one production line corresponding to any one procedure segment among a plurality of procedure segments during the process of producing the iron and steel product only receives raw material provided by one production line corresponding to the previous one procedure segment of the any one procedure segment, the fusing corresponding the plurality of third parameters using the procedure succession relation may include calculating a weighted sum of the third parameter reflecting the technical capability of the one production line corresponding to the previous one procedure segment and the third parameter reflecting the technical capability of the one production line corresponding to the any one procedure segment. When the one production line corresponding to the any one procedure segment receives raw materials provided by a plurality of production lines corresponding to previous one procedure segment, the fusing corresponding the plurality of third parameters using the procedure succession relation may include: assigning a weight to the third parameter reflecting the technical capability of each of a plurality of production lines corresponding to the previous one procedure segment according to a supply ratio of a raw material provided by each of a plurality of production lines corresponding to the previous one procedure segment to the one production line corresponding to the any one procedure segment, respectively; calculating a first weighted sum of a plurality of third parameters reflecting the technical capabilities of a plurality of production lines corresponding to the previous one procedure segment, respectively; and calculating a second weighted sum of a third parameter reflecting the technical capability of the one production line corresponding to the any one procedure segment and the first weighted sum.

According to exemplary embodiments of the present disclosure, a plurality of third parameters may include a plurality of melting-casting production line parameters and a specific thermoforming production line parameter, and a plurality of melting-casting production lines corresponding to the plurality of melting-casting production line parameters all may provide raw material for producing the iron and steel product to a specific thermoforming production line corresponding to the specific thermoforming production line parameter.

According to exemplary embodiments of the present disclosure, a plurality of third parameters may include a specific melting-casting production line parameter and a specific thermoforming production line parameter, and a specific melting-casting production line corresponding to the specific melting-casting production line parameter may provide raw material for producing the iron and steel product to a specific thermoforming production line corresponding to the specific thermoforming production line parameter.

According to exemplary embodiments of the present disclosure, a plurality of third parameters may include a plurality of melting-casting production line parameters and a plurality of thermoforming production line parameters, and a plurality of melting-casting production line parameters and a plurality of thermoforming production line parameters may correspond to a plurality of melting-casting production lines and a plurality of thermoforming production lines for producing the iron and steel product, respectively. The fusing the plurality of third parameters includes: assigning a weight to the melting-casting production line parameter corresponding to the corresponding melting-casting production line and to the thermoforming production line parameter corresponding to the corresponding thermoforming production line, respectively, according to a yield of each melting-casting production line and a yield of each thermoforming production line.

According to exemplary embodiments of the present disclosure, a plurality of third parameters may include at least one of melting-casting production line parameters and at least one of thermoforming production line parameters. The at least one melting-casting production line parameter and the at least one thermoforming production line parameter may correspond to at least one melting-casting production line and at least one thermoforming production line for producing the iron and steel product, respectively. The fusing the plurality of third parameters may include: fusing the melting-casting production line parameter corresponding to each melting-casting production line with the thermoforming production line parameter corresponding to each thermoforming production line which receives billet provided by the each melting-casting production line, respectively, to obtain a plurality of fusion values; and using a maximum fusion value among the plurality of fusion values as the top technical capability parameter of production line equipment.

According to exemplary embodiments of the present disclosure, a first-type second parameter in the at least one second parameter corresponding to the intrinsic parameter may include the product batch statistical parameter.

According to exemplary embodiments of the present disclosure, a plurality of third parameters may include a property dispersion parameter and a property average level parameter. The property dispersion parameter may represent dispersion of batch property statistical data of the iron and steel product, and the property average level parameter may represent an average level of batch property statistical data of the iron and steel product.

According to exemplary embodiments of the present disclosure, the fusing may include calculating a weighted sum.

According to exemplary embodiments of the present disclosure, the method may further include determining a quality level of the iron and steel product based on any one specified parameter selected from respective first parameters, respective second parameters and respective third parameters.

According to exemplary embodiments of the present disclosure, the determining a quality level of the iron and steel product based on any one specified parameter may include: when the any one specified parameter is larger than or equal to Ra, determining a quality level of the iron and steel product to be a first level; when the any one specified parameter is larger than or equal to Rb and is less than Ra, determining a quality level of the iron and steel product to be a second level; when the any one specified parameter is less than Rb and is larger than or equal to Rc, determining a quality level of the iron and steel product to be a third level; and when the any one specified parameter is less than Rc, determining a quality level of the iron and steel product to be a fourth level, where Ra>Rb>Rc. The quality of the iron and steel product of the first level is better than the quality of the iron and steel product of the second level, the quality of the iron and steel product of the second level is better than the quality of the iron and steel product of the third level, and the quality of the iron and steel product of the third level is better than the quality of the iron and steel product of the fourth level.

According to exemplary embodiments of the present disclosure, Ra may be set to 0.9, Rb may be set to 0.75 and Rc may be set to 0.60.

According to exemplary embodiments of the present disclosure, when quality levels of more than or equal to a specified number of a plurality of iron and steel products are to be determined, the any one specified parameter corresponding to each iron and steel product may be obtained, respectively. The determining quality levels of a plurality of iron and steel products based on the any one specified parameter may include: ranking specified parameters larger than or equal to Rd included in any one specified parameter of a plurality of iron and steel products; when a ranking proportion of the any one specified parameter of any one iron and steel product of the plurality of iron and steel products is less than or equal to aa %, determining the quality level of the any one iron and steel product to be a first level; when the ranking proportion of the any one specified parameter of any one iron and steel product is less than or equal to bb % and is larger than aa %, determining the quality level of the any one iron and steel product to be a second level; and when the ranking proportion of the any one specified parameter in any one iron and steel product is larger than or equal to bb % or the any one specified parameter of the any one iron and steel product is less than Rd, determining the quality level of the any one iron and steel product to be a third level, where bb %>aa %. The ranking proportion of the any one specified parameter of any one iron and steel product indicates: (a ranking number of the any one specified parameter of the any one iron and steel product/a total number of the any one specified index parameter involved in ranking and included in the any one specified parameter of the plurality of iron and steel products)×100%. The quality of the any one iron and steel product of the first level is better than the quality of the any one iron and steel product of the second level, and the quality of the any one iron and steel product of the second level is better than the quality of the any one iron and steel product of the third level.

According to exemplary embodiments of the present disclosure, aa % may be set to 15%, bb % may be set to 70% and Rd may be set to 0.60.

According to exemplary embodiments of the present disclosure, the calculating the evaluation processing data may include: performing a standardizing process for the multiple types of data using a standardization function to obtain standardization data; and performing an evaluation process for the standardization data using the evaluation function to obtain the evaluation processing data.

According to one aspect of the present disclosure, a device for determining a quality level of an iron and steel product may include a processor which may be configured to obtain a plurality of first parameters related to the quality of an iron and steel product; fuse the plurality of first parameters to obtain a comprehensive quality evaluation parameter; and determine a quality level of the iron and steel product based on the comprehensive quality evaluation parameter.

DETAILED DESCRIPTION OF EXEMPLARY EMBODIMENTS

Embodiments of the present disclosure are now more sufficiently described with reference to the accompany drawings, in which exemplary embodiments of the present disclosure are illustrated. However, the present disclosure may be implemented in many different forms, rather than being construed as being limited to these embodiments described herein. On the contrary, these embodiments are provided so that the present disclosure will be complete and integrate, and the concept of the embodiments of the present disclosure will be sufficiently conveyed to those ordinary skilled in the art by these embodiments. Multiple specific details are set forth in the form of examples in the following detailed description to provide enough comprehension for the related teaching.

The method and device for determining a quality level of an iron and steel product according to the concept of the present disclosure will be particularly described below with reference to the drawings.

Figure 1:
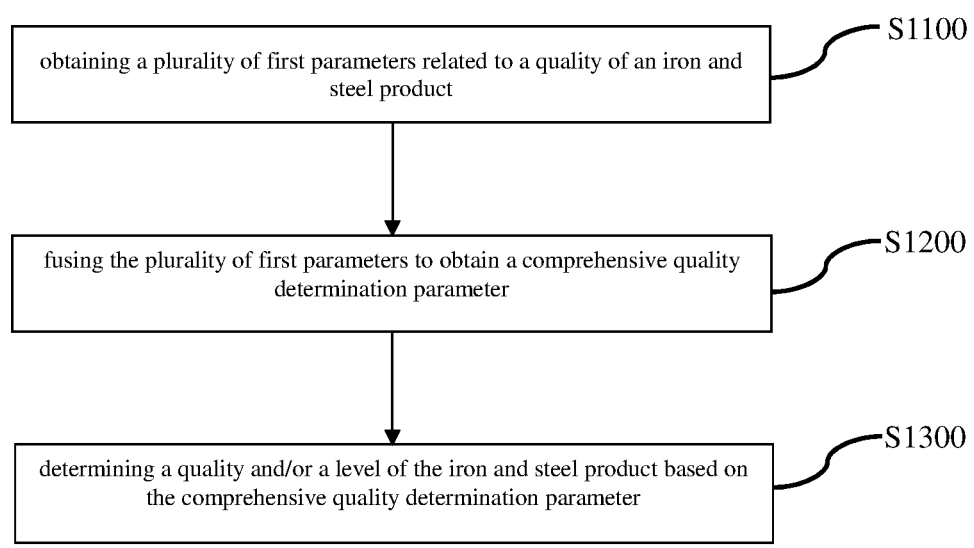
FIG. 1 is a flow diagram illustrating a method for determining a quality level of an iron and steel product in accordance with the inventive concept.
Figure 2:
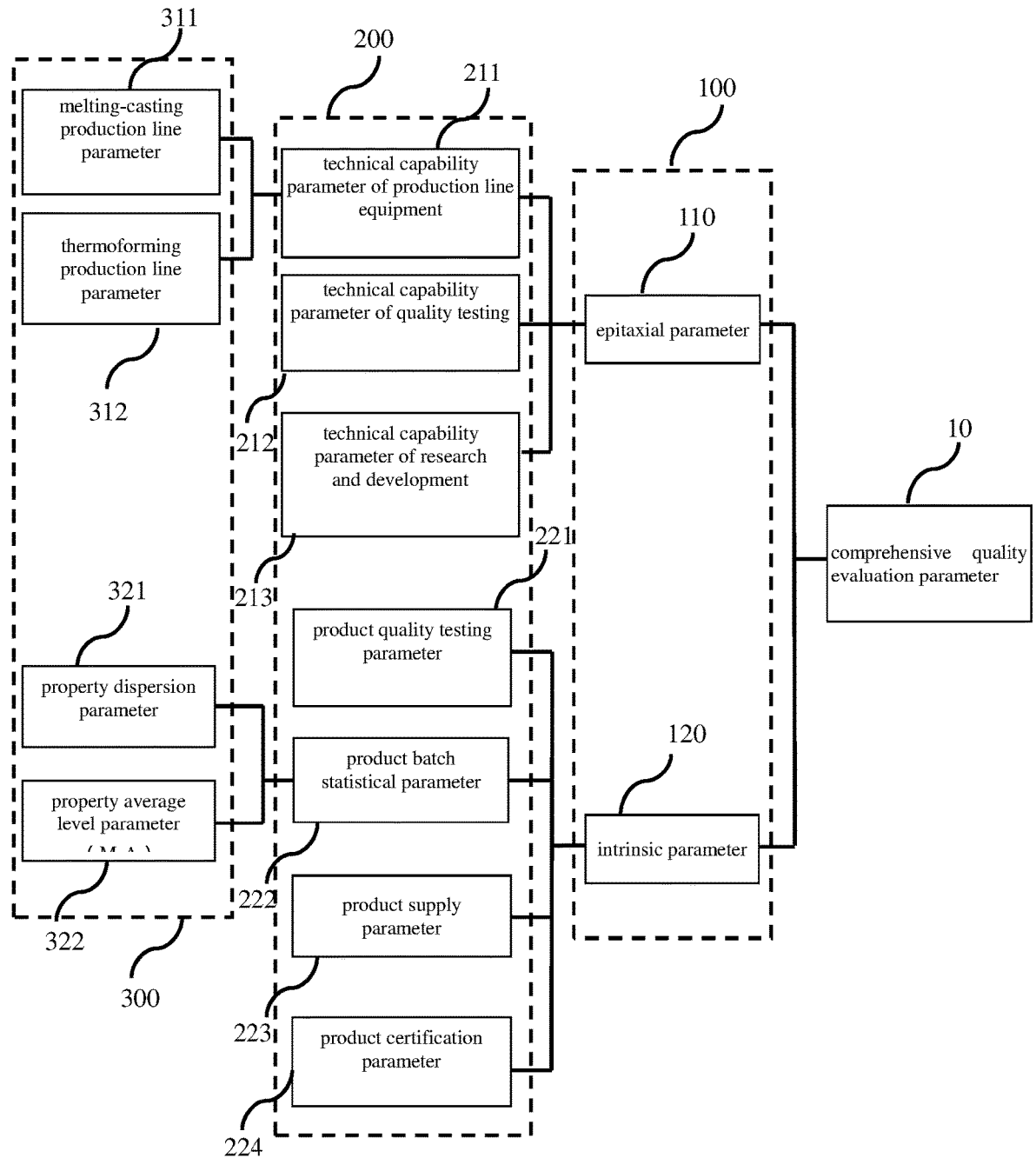
FIG. 2 is schematic flow diagram illustrating obtaining each parameter for determining a quality level of an iron and steel product in accordance with the inventive concept.
Figure 3:
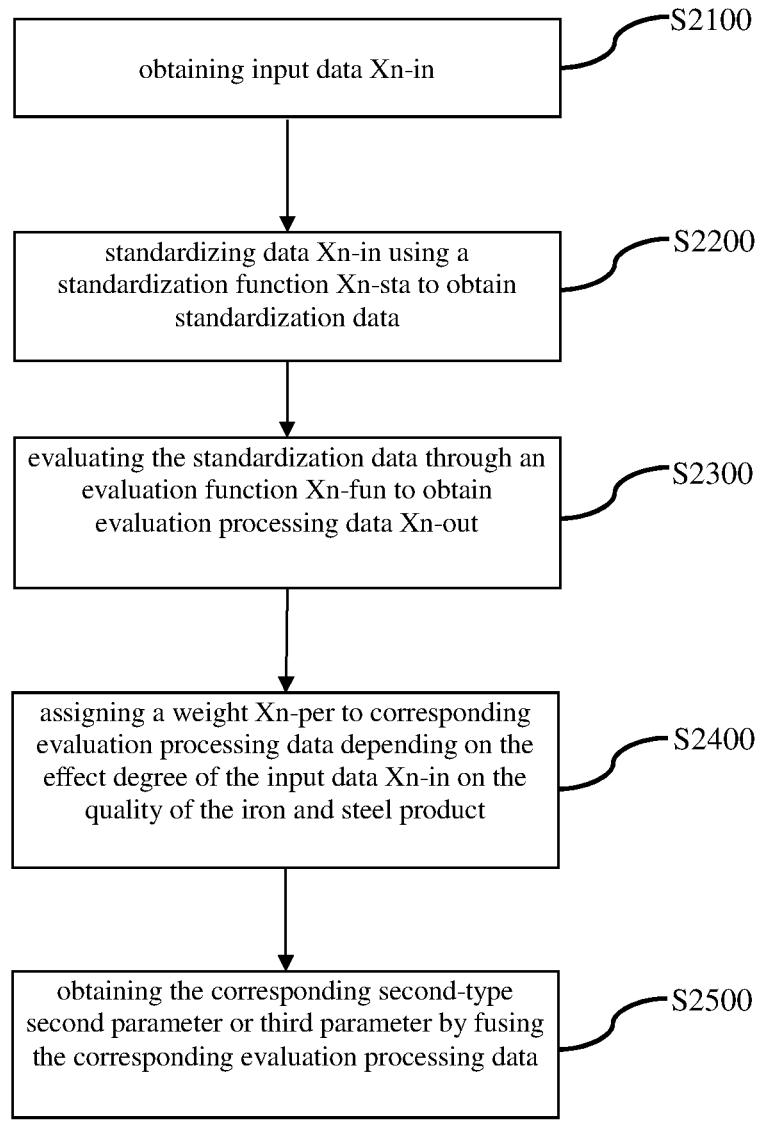
FIG. 3 is a flow diagram illustrating process of multiple types of data corresponding to respective parameters.

FIG. 1 is a flow diagram illustrating a method for determining a quality level of an iron and steel product in accordance with the inventive concept. FIG. 2 is schematic flow diagram illustrating obtaining each parameter for determining a quality level of an iron and steel product in accordance with the inventive concept. FIG. 3 is a flow diagram illustrating process of multiple types of data corresponding to respective parameters.

As illustrated in FIGS. 1 and 2, the method for determining a quality level of an iron and steel product may include: obtaining a plurality of first parameters 100 related to the quality of an iron and steel product (S1100); fusing the plurality of first parameters 100 to obtain a comprehensive quality evaluation parameter 10 (S1200); and determining a quality level of the iron and steel product based on the comprehensive quality evaluation parameter 10 (S1300).

In the exemplary embodiments according to the present disclosure, as illustrated in FIG. 2, the above plurality of first parameters 100 may include an intrinsic parameter 120 which is a parameter reflecting the property of the iron and steel product itself. Although the intrinsic parameter 120 may be a parameter which directly or indirectly reflects the property of the iron and steel product itself, of the iron and steel product, the product quality further strongly depends on production equipments and production lines of a steel producer. It may be understood that production equipments and production lines having excellent qualities produce a positive promotion effect on and have a correlation with producing products with excellent qualities. In addition, the higher redundancy of the production testing technical level and capability of a producer is, the larger a control latitude for the product quality is, and accordingly more easily a benign closed loop of "produce→detect→feedback→adjust and re-produce" is formed inside the production enterprise. Such a mechanical closed loop may perform effective optimization and acceleration functions to facilitate steady improvement of product qualities through excellent research mechanism and level of an enterprise. This type of soft power involving testing capability and research level also exert an influence on qualities of iron and steel products to a extent. Therefore, a quality level of a product can be more sufficiently and truly reflected only by comprehensively considering the property of the product itself and other factors having an impact on the quality of the product, when determining the quality level of an iron and steel product.

Thus, in the exemplary embodiments according to the present disclosure, the above plurality of first parameters 100 may further include an epitaxial parameter 110 which has an impact on the quality of the iron and steel product. The epitaxial parameter 110 represents a parameter which reflects research and development capability of a manufacturer of the iron and steel material and/or technical capabilities of respective technological processes during a process of producing the iron and steel material.

As seen from above, compared with a conventional two-value system, in the exemplary embodiments according to the present disclosure, when a quality level of the iron and steel product is determined, the comprehensive quality evaluation parameter 10 for determining a quality level of the iron and steel product is obtained through organic fusion of the above intrinsic parameter 120 and the epitaxial parameter 110, thereby a quality level of the iron and steel product may be more sufficiently and truly reflected. However, exemplary embodiments according to the present disclosure are not limited hereto. For example, the processor may be further configured to determine a quality level of the iron and steel product based on any one parameter among the plurality of first parameters 100, and particularly, a quality level of the iron and steel product may be determined based on any one parameter of the intrinsic parameter 120 and the epitaxial parameter 110. As such, diversity demands of different users may be satisfied.

Steps performed by the above processor are particularly described below in conjunction with FIGS. 1 and 2.

For step S1100 for obtaining the plurality of first parameters 100, each of the first parameters 100 may be obtained through corresponding at least one of second parameters 200. Particularly, when each of the first parameters 100 may be obtained through corresponding a plurality of second parameters 200, the first parameter 100 may be calculated by fusing corresponding the plurality of second parameters 200, and when each of the first parameters 100 may be obtained through corresponding one of the second parameters 200, the corresponding one second parameter 200 may be directly used as the first parameter 100. In addition, fusing corresponding the plurality of second parameters 200 may indicate calculating a weighted sum of the plurality of second parameters 200, wherein when the weighted sum of the plurality of second parameters 200 is calculated, a weight assigned to each second parameter 200 is proportional to an effect degree of the second parameter 200 on the quality of the iron and steel product. However, the concept of the present invention is not limited hereto, and the second parameters may be further fused through other means.

Particularly, as illustrated in FIG. 2, the plurality of second parameters 200 corresponding to the intrinsic parameter 120 among the plurality of first parameters 100 may include at least one parameter of a product quality testing parameter 221, a product batch statistical parameter 222, a product supply parameter 223 and a product certification parameter 224. However, the above parameters are only exemplary, and other parameters which are parameters reflecting the property of the iron and steel product itself may be further used. Wherein the product batch statistical parameter 222 may be a parameter reflecting quality stability and an average level of the iron and steel product and obtained based on batch statistical data of the iron and steel product produced by the production line of the iron and steel product during a period of time, the product quality testing parameter 221 may be a parameter directly reflecting the quality of the iron and steel product and obtained based on property testing data of the iron and steel product, the product supply parameter 223 may be a parameter indirectly reflecting the product quality and obtained based on data associated with supply achievements of the iron and steel product, and the product certification parameter 224 may be a parameter indirectly reflecting the product quality and obtained based on third party certification data of the iron and steel product.

For the second parameter 200 corresponding to the intrinsic parameter 120, the second parameter 200 may be classified into a first-type second parameter and a second-type second parameter according to the method for obtaining the second parameter 200. Wherein the first-type second parameter may be obtained by fusing corresponding a plurality of third parameters 300, and the second-type second parameter may be obtained through corresponding multiple types of data. In addition, similar to the second-type second parameter, the third parameter may also be obtained through corresponding multiple types of data.

Particularly, the above multiple types of data related to the quality of the iron and steel product usually need to be obtained, in order to accurately determine a quality level of the iron and steel product. However, since the multiple types of data generally have different orders of magnitude, dimensions, and the like due to different characters thereof, the quality level of the iron and steel product cannot be correctly reflected by simply fusing multiple types of data. Thus, in order to ensure reliability of the result, it is necessary to perform certain processes for the above multiple types of data before obtaining the corresponding second-type second parameter or third parameter through the above multiple types of data. Below the process of multiple types of data will be particularly described with reference to FIG. 3.

In the exemplary embodiments according to the present disclosure, as illustrated in FIG. 3, obtaining the second-type second parameter or the third parameter through the multiple types of data includes: obtaining multiple types of data corresponding to each second-type second parameter or each third parameter for calculating the intrinsic parameter, and using each type of data as input data Xn-in (S2100); processing different types of data using a standardization function Xn-sta to obtain standardization data (S2200); processing the standardization data corresponding to the input data Xn-in through an evaluation function Xn-fun to obtain evaluation processing data Xn-out capable of being used to more accurately determine the quality level of the iron and steel product (S2300); assigning a corresponding weight Xn-per to corresponding evaluation processing data depending on the effect degree of the input data Xn-in on the quality of the iron and steel product (S2400); and obtaining the corresponding second-type second parameter or third parameter by fusing the corresponding evaluation processing data (S2500). However, exemplary embodiments according to the concept of the present disclosure are not limited thereto, for example, the processing multiple types of data using a standardization function may be omitted in another embodiment according to the present disclosure. Wherein different types of data Xn-in may include different standardization functions Xn-sta and different evaluation functions Xn-fun, wherein the standardization functions Xn-sta may non-dimensionalize data or standarlize data indexes of different levels of products (such as, the products with yield strengths of 355 MPa grade, 460 MPa grade), thereby facilitating simplification and uniformity of evaluation functions Xn-fun, and the evaluation functions Xn-fun may be used for obtaining numerical results for performing quantitative description and evaluation on the indexes.

In addition, fusing the corresponding evaluation processing data may indicate calculating a weighted sum of evaluation processing data, wherein when the weighted sum of the evaluation processing data is calculated, a weight assigned to the evaluation processing data is proportional to an effect degree of input data Xn-in corresponding to the evaluation processing data on the quality level of the iron and steel product. However, the concept of the present disclosure is not limited hereto, for example, the embodiments according to the concept of the present disclosure may further include other fusion means which can appropriately reflect an effect of various types of data on the quality level of the iron and steel product.

As seen from above, each second parameter 200 corresponding to the intrinsic parameter corresponds to multiple types of data.

Multiple types of data corresponding to the product quality testing parameter 221 may be testing data obtained by testing the iron and steel product based on a technical standard, a supply condition, or the like with respect to the iron and steel product. However, exemplary embodiments according to the present disclosure are not limited hereto, for example, types of testing data may also be determined according to demands of users. Any one iron and steel product has a corresponding technical standard or a supply technical agreement, for example, ship-hull steel generally satisfies a requirement of Chinese national standard GB 712 in China, pipeline steel generally satisfies a requirement for American Petroleum Institute API 5L, and some products further need to satisfy more strict technical agreement. For example, multiple types of data corresponding to the product quality testing parameter 221 may include chemical component data such as, for example, S, P, C, Si, Mn, and the like, and mechanical property data such as, for example, yield strength, tensile strength, elongation, cold bending property, impact energy, and the like. However, exemplary embodiments according to the present disclosure are not limited thereto.

Multiple types of data corresponding to the product batch statistical parameter 222 may correspond to batch statistical data of the iron and steel product produced during a period of time. Wherein the data types in batch statistical data may be determined according to user demands or corresponding technical standards. The quality level of the product within a period of time may be intuitively evaluated through an analysis for the batch statistical data of the iron and steel product within the period of time. Such batch statistical data may avoid instability of evaluation caused by performance fluctuation of a single product on one hand and may provide a quantitative index for evaluating stability of the product quality of an enterprise on the other hand. In the exemplary embodiments according to the present disclosure, such the batch statistical data may be provided by a quality management system (such as Manufacturing Execution System MES or Enterprise Resource Planning ERP system) of an enterprise and may also be provided by the testing of a second party (user) or third party organization. Data from different sources may further complement and confirm each other.

The determination for the quality level of the iron and steel product may further consider information such as third party certification, supply performance, and the like. Particularly, quality information of the iron and steel product indirectly reflected by third party certification and supply performance is reflected through the product supply parameter 223 and the product certification parameter 224. Wherein supply achievement (i.e., supply quantity) within a period of time may indirectly reflect the quality of a product to an extent. Certification information may further reflect the quality level of the product through a third party, and the certification information specifically includes but is not limited to time of certification, certification level, certification variety, certification size range, and the like.

In addition, in a plurality of second parameters 200 corresponding to the intrinsic parameter 120, the first-type second parameter may include the product batch statistical parameter 222. A plurality of third parameters 300 corresponding to the batch statistical parameter 222 may include a property dispersion parameter 321 and a property average level parameter 322. Wherein the property dispersion parameter 321 may be a parameter representing dispersion of batch property statistical data of the iron and steel product, and the property average level parameter 322 may be a parameter representing an average level of batch property statistical data of the iron and steel product.

In addition, as illustrated in FIG. 2, at least one second parameter 200 corresponding to the epitaxial parameter 110 among the plurality of first parameters 100 may include at least one parameter of a technical capability parameter of production line equipment 211, a technical capability parameter of quality testing 212 and a technical capability parameter of research and development 213. However, the above parameters are only exemplary, and other parameters which generate an effect on the quality of the iron and steel product may be further used. The technical capability parameter of production line equipment 211 may be a parameter reflecting the production line equipment technical capability, and obtained through data associated with production equipments and production process parameters of iron and steel products corresponding to respective technological processes during a productive process for producing the iron and steel product. The technical capability parameter of quality testing 212 may be a parameter reflecting the enterprise testing technical capability, and obtained through data associated with testing equipments and technical capabilities for testing iron and steel products during a productive and testing process for producing the iron and steel product. The technical capability parameter of research and development 213 may be a parameter reflecting the enterprise research and development technical capability, and obtained through data associated with research and development capability of the production enterprise which produces the iron and steel product.

For the second parameter 200 corresponding to the epitaxial parameter 110, the second parameter 200 may also be classified into a first-type second parameter and a second-type second parameter according to the method for obtaining the second parameter 200. The methods for obtaining the first-type second parameter and the second-type second parameter are the same as the methods for obtaining the second parameter 200 corresponding to the intrinsic parameter 120 described above, and no more detailed description is given herein.

As seen from above, each second parameter 200 corresponding to the epitaxial parameter 110 corresponds to multiple types of data.

Particularly, for a certain iron and steel product, a good hot metal pretreatment equipment and procedure, an excellent melting-casting and refining equipment, a control means for segregation in continuous casting, and the like are all origins for obtaining the excellent billet/slab (raw material) quality. Moreover, means like a billet/slab heating furnace, high pressure water descaling, a controlled rolling and cooling means, a straightening machine, a heat treatment equipment, and the like in the thermoforming production line are especially direct origins of the final quality of a product. The technical capability parameter of production line equipment 211 may readily reflect the above impact factors into the determination for a quality level of the iron and steel product directly. In the exemplary embodiments according to the present disclosure, multiple types of data corresponding to the technical capability parameter of production line equipment 211 may include but are not limited to related data of a casting method, a hot metal of blast furnace (presence/absence), a hot metal pretreatment, average capacity of steel making furnaces, whether there is secondary refining, a vacuum degassing method, a maximum slab thickness, minimum contents of impurity elements such as S, P, O, N, and the like in a practical operation process, a ladle gas analysis equipment, whether there is a wire feeding process, a casting superheat and fluctuation range, whether there is a control equipment for segregation in continuous cast, a slow cooling pit (presence, absence and/or with the heating), a type of heating furnace, upper/lower limit of a temperature controllable zone of a heat preservation section of a heating furnace, the pressure value for the high pressure water descaling, a maximum opening degree of a mill, a maximum rolling force of a rolling mill, a motor power, the thinnest and thickest supply thickness and the like. As for the type of data such as the hot metal of blast furnace (presence/absence), a vacuum degassing method or a slow cooling pit (presence, absence and/or with the heating), numeralization may also be made thereto. For example, presence of a slow cooling pit may be represented by a number 1, and absence of a slow cooling pit may be represented by a number 0. However, exemplary embodiments according to the present disclosure are not limited thereto. Digital evaluation may be performed for respective key procedures and equipment technical capabilities of the production line of the iron and steel product through the above different types of data. This is helpful to understand internal logic of a final quality level of the product, and is also an important evidence for the final quality of the product.

In addition, as seen from above, the soft power involving testing capability and research level may also be evaluated through numerical indexes to an extent and is reflected into the quality level of product of a production enterprise. Particularly, in the exemplary embodiments according to the present disclosure, multiple types of data corresponding to the technical capability parameter of quality testing 212 may include but are not limited to related data of a maximum energy for impact test, a minimum temperature for impact test, a maximum tonnage of tensile test, a maximum temperature of tensile test, whether there is a drop weight test machine and a maximum energy thereof, whether there is a fracture toughness (such as Crack Tip Open Displacement CTOD) test machine, and the like. In addition, multiple types of data corresponding to the technical capability parameter of research and development 213 may include but are not limited to China. National Accreditation Service CNAS certification, American Petroleum institute API certification, an contract amount associated with research and development for last year, a certification level of a research and development department, the staff number of a research and development department, the number of senior or above research and development staff of the research and development department, the number of patents which were granted for last year, the number of melting furnaces for laboratorial research, a minimum and maximum furnace capacity of melting furnaces for laboratorial research, a rolling machine for laboratorial research (presence/absence) and the like. The above multiple types of data may be used for performing numerical evaluation for the enterprise detection technical capability and the research and development capability, respectively, and may relatively and objectively reflect average capability and level of the product quality reliability of a producing enterprise within a period of time in conjunction with the evaluation for the production line equipment technical capability.

The method for processing the above multiple types of data is the same as the method for processing the multiple types of data when calculating the intrinsic parameter 120, and thus, no more detailed description is given herein.

In addition, in the plurality of second parameters 200 corresponding to the epitaxial parameter 110, the first-type second parameter may include the technical capability parameter of production line equipment 211. A plurality of third parameters 300 corresponding to the technical capability parameter of production line equipment 211 correspond to relatively independent segmented production lines corresponding to multiple process segments during the process of producing the iron and steel product, respectively, wherein one third parameter only corresponds to one segmented production line and reflects the technical capability of the corresponding production line. In practical production, the iron and steel material may be subject to production lines including but not limited to a melting-casting production line, a thermoforming production line, a heat treatment production line, a working production line, and the like in order so as to obtain a final iron and steel product. However, an order of production lines according to the present disclosure is not limited thereto. The working production line may further include a cold working production line and a welding production line. For example, working production line of steel pipes for pipelines used to transport oil and natural gas may include a cold working production line and a subsequent welding production line simultaneously. For a specific product, a case where a plurality of production lines of the same type are applied simultaneously generally exists. For example, a plurality of melting-casting production lines and a plurality of thermoforming production lines are simultaneously applied, and at this point, the system is comparatively complicated. The equipment technical capabilities of production lines are not the same. This makes it difficult to perform numerical evaluation for the equipment technical capability of the production lines. In the exemplary embodiments according to the present disclosure, this problem is solved according to the method of "procedure succession" proposed by the present disclosure. In the embodiments according to the present disclosure, the process of fusing evaluation processing data corresponding to any one second parameter or third parameter may be called as "procedure evaluation", and the represented object corresponding to each second parameter or third parameter may be called as a procedure. For example, melting-casting and thermoforming are all procedures said in the present disclosure, and moreover, product certification and supply, product batch statistics, and the like when being involved in representation and evaluation may also be called as procedures.

Particularly, for a certain production line corresponding to a certain procedure segment, if the billet/slab (raw material) thereof comes from a plurality of production lines corresponding to the previous one procedure segment or it provides a raw material to a plurality of production lines corresponding to the next one procedure segment, the quality of the raw material of the certain production line corresponding to a certain procedure segment succeeds from a plurality of production lines corresponding to the previous one procedure segment, or the quality of the raw material of the certain production line is inherited/succeeded by the plurality of production lines corresponding to the next one procedure segment. Thus, when performing numerical evaluation for the equipment technical capability of a production line, the third parameter 300 reflecting the technical capabilities of a plurality of production lines corresponding to the previous one procedure segment needs to be assigned with a weight according to a raw material supply ratio of providing a raw material to the certain production line (for example, a weight assigned to the third parameter 300 is proportional to a supply ratio of providing a raw material to the certain production line by the production line corresponding to the third parameter 300), then a weighted sum of the third parameter 300 reflecting the technical capabilities of the plurality of production lines corresponding to the previous one procedure segment is calculated, so as to fuse the weighted sum with the third parameter 300 reflecting the production line corresponding to other process segment to obtain the technical capability parameter of production line equipment 211. For example, for a certain thermoforming production line, if the source of billet/slab (raw material) thereof is not unique, the quality of billet/slab thereof inherits/succeeds from the melting-casting production line, and thus, the level of billet/slab will be determined by weighting according to a billet/slab supply ratio by evaluation results of different melting-casting production lines for producing the product. Similarly, if a certain product comes from a different thermoforming production line, the thermoforming equipment level is determined by weighting according to a product supply ration by an evaluation result of the thermoforming production line.

Figure 4A:
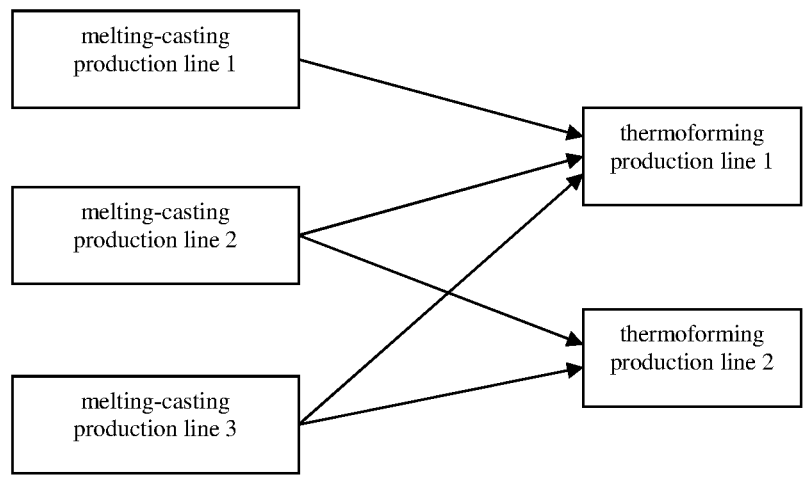
FIG. 4A is a schematic diagram illustrating a plurality of melting-casting production lines and a plurality of thermoforming production lines.
Figure 4B:
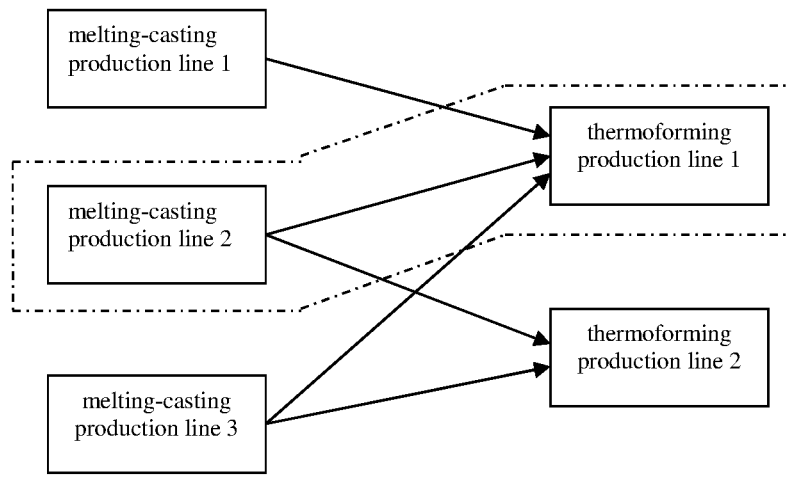
FIG. 4B is a schematic diagram illustrating a specific melting-casting production line and a specific thermoforming production line.
Figure 4C:
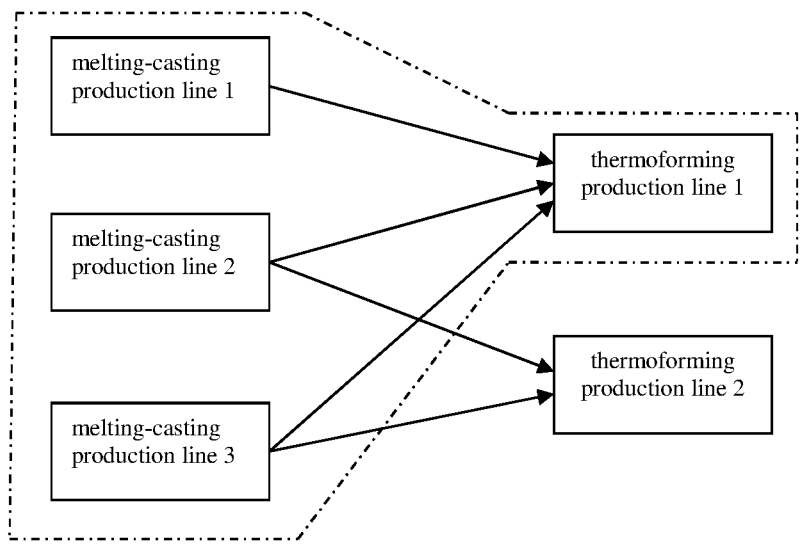
FIG. 4C is a schematic diagram illustrating a specific thermoforming production line and a plurality of melting-casting production lines.
Figure 4D:
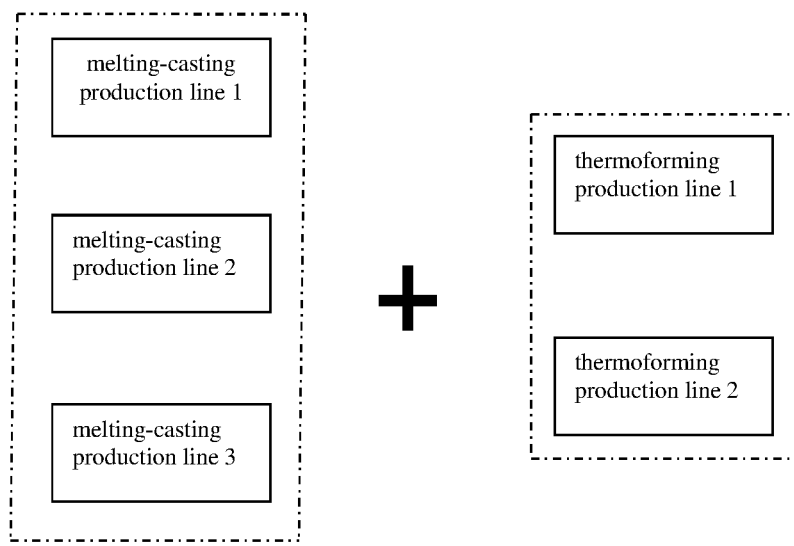
FIG. 4D is a production line diagram illustrating obtaining an enterprise equipment technical average level.

The method for obtaining the technical capability parameter of production line equipment 211 will be particularly described below in combination with FIGS. 4A-4D and taking a plurality of third parameters 300 corresponding to the technical capability parameter of production line equipment 211 only including melting-casting production line parameter(s) 311 and thermoforming production line parameter(s) 312 as an example. Wherein FIG. 4A is a schematic diagram illustrating a plurality of melting-casting production lines and a plurality of thermoforming production lines. FIG. 4B is a schematic diagram illustrating a specific melting-casting production line and a specific thermoforming production line. FIG. 4C is a schematic diagram illustrating a specific thermoforming production line and a plurality of melting-casting production lines. FIG. 4D is a production line diagram illustrating obtaining an enterprise equipment technical average level.

There are generally five methods for calculating the technical capability parameter of production line equipment 211 as follows:

(1) A specific melting-casting production line+a specific thermoforming production line: which is similar to the case of a single melting-casting production line and a single thermoforming production line, and is a special case of applying a procedure succession relation. FIG. 4A illustrates a case including a plurality of melting-casting production lines and a plurality of thermoforming production lines. A dashed frame of FIG. 4B illustrates a specific melting-casting production line 2 and a specific thermoforming production line 1, wherein the specific melting-casting production line and the thermoforming production line are generally required to be associated with each other. That is, the specific melting-casting production line directly provides billet/slab (raw material) to the specific thermoforming production line, otherwise, there is no practical significance. For example, melting-casting production line 1 and thermoforming production line 2 as illustrated in FIG. 4B are not associated with each other, which are not generally used for calculating the technical capability parameter of production line equipment 211 simultaneously. In such a case, the technical capability parameter of production line equipment 211 is calculated by fusing the specific melting-casting production line parameter corresponding to the specific melting-casting production line and the specific thermoforming production line parameter corresponding to the specific thermoforming production line.

(2) A plurality of melting-casting production lines+a specific thermoforming production lines: regarding the production line combination as illustrated in the dashed frame of FIG. 4C, melting-casting production lines 1 to 3 provide billet/slab (raw material) to the thermoforming production line 1 simultaneously, and in such a case, the technical capability parameter of production line equipment 211 needs to be calculated according to "a procedure succession", wherein the level of billet/slab from the thermoforming production line is obtained by weighting the evaluation results of different melting-casting production lines practically supplying billet/slab according to a billet/slab supply ratio. Thus, a weight needs to be assigned to melting-casting production line parameters corresponding to different melting-casting production lines according to a ratio of providing billet/slab to the specific thermoforming production line by different melting-casting production lines (for example, a weight assigned to different melting-casting production line parameters is proportional to a ratio of providing billet/slab (raw material) to the specific thermoforming production line by the melting-casting production lines corresponding to the parameters), and a weighted sum of melting-casting production line parameters corresponding to different melting-casting production lines is calculated. Then the weight sum is fused with the specific thermoforming production line parameter (for example, a weighted sum of the weighted sum and the specific thermoforming production line parameter is calculated again, wherein when calculating a weighted sum again, the weight assigned to the previous one weighted sum or the weight assigned to the specific thermoforming production line parameter is proportional to the effect of the production line corresponding to the previous weighted sum or the specific thermoforming production line parameter on the quality of the iron and steel product), so as to calculate the technical capability parameter of production line equipment 211. For example, the technical capability parameter of production line equipment E(for E–$R_i$) with respect to the thermoforming production line $R_i$ may be calculated in the following equation:

$$E(\text{for } E - R_i) = (E - R)_i + \sum_{j=1}^{n}(E - M)_j P_j$$

where E(for E–$R_i$) represents the technical capability parameter of production line equipment 211 with respect to the thermoforming production line $R_i$; (E–M)$_j$(j=1, 2, ..., n) represents the melting-casting production line parameter corresponding to the melting-casting production line which practically provides billet/slab to the thermoforming production line $R_i$ and the corresponding billet/slab supply ratio is $P_j$, and $$\sum_{j=1}^{n} P_j = 1;$$

(E–R)$_i$ represents the specific thermoforming production line parameter corresponding to the specific thermoforming production line $R_i$.

(3) Enterprise equipment technical average level: as illustrated in FIG. 4D, for a specific product, in the case where the thermoforming production line and the melting-casting production line of the previous procedure thereof are not determined, the iron and steel materials are generally assigned randomly according to respective yields of the thermoforming production line and the melting-casting production line. In such a case, a weight needs to be assigned to the melting-casting production line parameter corresponding to the corresponding melting-casting production line and the thermoforming production line parameter corresponding to the corresponding thermoforming production line according to respective yields of the melting-casting production line and the thermoforming production line (for example, the weight assigned to the above parameters is proportional to a ratio of yields of the production lines corresponding to the corresponding parameters to a total yield), and then the melting-casting production line parameter corresponding to the melting-casting production line is fused with the thermoforming production line parameter corresponding to the thermoforming production line (for example, fusing the above parameters represents calculating a weighted sum, however, the concept of the present disclosure is not limited thereto, and the parameters mentioned above may also be fused through other methods) to obtain the technical capability parameter of production line equipment 211 reflecting an average strength of producing the product of the enterprise. For example, the technical capability parameter of production line equipment 211 reflecting an average strength of producing the product of the enterprise may be calculated in the following equation:

$$E_{ave} = \sum_{i=1}^{n}(E - R)_i P_i + \sum_{j=1}^{n}(E - M)_j P_j$$

where $E_{ave}$ represents the technical capability parameter of production line equipment 211 reflecting an average strength of producing the product of the enterprise; (E–M)$_j$(j=1, 2, ..., n) represents the melting-casting production line parameter corresponding to the melting-casting production line of producing the iron and steel product, and the corresponding billet supply ratio is $P_j$, and $$\sum_{j=1}^{n} P_j = 1;$$

$(E-R)_i (i=1, 2, \ldots, m)$ represents the thermoforming production line parameter corresponding to the thermoforming production line of producing the iron and steel product, and the corresponding supply ratio is $P_i$, and $$\sum_{i=1}^{m} P_i = 1.$$

(4) Optimum production line equipment technical level: a production line with the optimum technical capability is selected from all melting-casting and thermoforming production lines, which are associated with each other, for producing the iron and steel product of the enterprise. Particularly, for all melting-casting production lines and thermoforming production lines, which are associated with each other, among all thermoforming production lines and all melting-casting production lines, the melting-casting production line parameter and the thermoforming production line parameter corresponding to each of all melting-casting production lines and thermoforming production lines in association with each other are fused (for example, fusing the above parameters represents calculating a weighted sum, wherein a weight assigned to respective parameters is proportional to the effect degree of the production lines corresponding to the parameters on the quality of the iron and steel product, however, the concept of the present disclosure is not limited thereto, and the above parameters may also be fused through other methods), to obtain a fusion value corresponding to each of melting-casting production lines and thermoforming production lines in association with each other, and the maximum fusion value among all fusion values is used as the optimum technical capability parameter of production line equipment 211 reflecting the optimal production state and product potential of the enterprise. For example, the technical capability parameter of production line equipment 211 reflecting the optimum production line equipment technical capability of producing the product of the enterprise may be calculated according to the following equation:

$$E_{max} = \underset{i=1, j=1}{\overset{m,n}{\text{MAX}}} [(E-R)_i + (E-M)_j]$$

where $E_{max}$ represents the technical capability parameter of production line equipment 211 reflecting the optimum production line equipment technical capability of producing the product of the enterprise; $(E-M)_j (j=1, 2, \ldots, n)$ represents the melting-casting production line parameter corresponding to the melting-casting production line for producing the iron and steel product; $(E-R)_i (i=1, 2, \ldots, m)$ represents the thermoforming production line parameter corresponding to the thermoforming production line for producing the iron and steel product, and the values of i and j are sequences of the melting-casting production lines and the thermoforming production lines which are associated with each other.

(5) A certain melting-casting production line provides billet/slab to a plurality of thermoforming production lines. Similar to the method in the above method (2), the subsequent product level of the melting-casting production line is obtained by weighting according to a billet supply ratio by corresponding parameters of different thermoforming production lines which practically complete production. Generally, such process is rarely used in practice.

When the second parameter obtained by a "procedure succession" mode is fused with other second parameter for determining a quality level of the product, all distinguishable attributes of the corresponding products are all subordinate to corresponding production line attributes. For example, the product evaluation content of the optimum production line is also obtained from the optimum production line rather than being doped with product content of other production line.

Next, after the third parameter, the second parameter, the first parameter and a product quality evaluation parameter are obtained by calculating according to the above method, a quality level of the iron and steel product may be determined according to any one specified parameter among the third parameter, the second parameter, the first parameter and the product quality evaluation parameter through a certain determination method. Obviously, diversity demands of different users may be satisfied while more sufficiently determining a quality level of the product through such a method for determining a quality level of the product. However, exemplary embodiments according to the concept of the present disclosure are not limited hereto, for example, a fourth parameter or more may be further expanded based on the above methods in another embodiment.

Particularly, in the exemplary embodiments according to the present disclosure, a quality level of the iron and steel product may be determined through a score determination method or a ranking determination method.

Wherein the specific steps of the score determination method are as follows:

when any one specified parameter is larger than or equal to Ra, determining a quality level of the iron and steel product to be a first level; when any one specified parameter is larger than or equal to Rb and is less than Ra, determining a quality level of the iron and steel product to be a second level; when any one specified parameter is less than Rb and is larger than or equal to Rc, determining a quality level of the iron and steel product to be a third level; and when any one specified parameter is less than Rc, determining a quality level of the iron and steel product to be a fourth level.

Wherein Ra>Rb>Rc, and quality of the first level to the fourth level of iron and steel products successively become worse. In addition, Ra, Rb and Rc may be particularly defined based on practical situations. For example, they may be set to be respectively: Ra=0.9, Rb=0.75, Rc=0.60.

Wherein the specific steps of the ranking determination method are as follows:

ranking specified parameters larger than or equal to Rd in any one specified parameter corresponding to a plurality of iron and steel products; when a ranking proportion of any one specified parameter of a certain iron and steel product of the plurality of iron and steel products is less than or equal to aa %, determining the quality level of the corresponding iron and steel product to be a first level; when the ranking proportion of any one specified parameter is less than or equal to bb % and is larger than aa %, determining the quality level of the corresponding iron and steel product to be a second level; and when the ranking proportion of any one specified parameter is larger than or equal to bb % or any one specified parameter is less than Rd, determining the quality level of the corresponding iron and steel product to be a third level. Wherein bb %>aa %, and the ranking proportion of any one specified parameter of a certain iron and steel product indicates: (a ranking number of any one specified parameter of a certain iron and steel product/a total number of any one specified parameter involved in ranking in any one specified parameter of the plurality of iron and steel products)×100%. In addition, qualities of the first level to the third level of iron and steel products successively become worse.

In practical application, values of aa % and bb % may be set according to actual needs. For example, they may be set to be aa=15, bb=70, respectively. For example, accumulative 25 products with the same kind participate in quality grading evaluation and are all qualified products. Then the products of top three are evaluated as the result of the first level, the fourth to seventeenth products are evaluated as the result of the second level, and the eighteenth to twenty-fifth products are evaluated as the result of the third level.

In practical application, the score determination method is adapted to separately evaluate a certain product or the less number of products involved in evaluation, and the ranking determination method is adapted to simultaneously evaluating a plurality of products provided by multiple suppliers.

Below the above method for determining a quality level of an iron and steel product is particularly described through specific embodiments.

Embodiment 1

Regarding three iron and steel makers X, Y and Z, random inspection is performed on a certain ship-hull plate to test the product quality of these enterprises. Quality levels of the samples by random inspection are determined based on the product quality testing parameter 221 through the equipment and method for determining a quality level of an iron and steel product according to the exemplary embodiments of the present disclosure. In order to calculate the product quality testing parameter 221, chemical components may be selected to be sulfur and phosphor, mechanical property may be selected to be yield strength, elongation and impact work, but the exemplary embodiments according to the present disclosure are not limited thereto. The practically measured content of sulfur element S, content of phosphor element P, value of yield strength ReH, elongation A and impact energy KV are input into a processor 120 as multiple types of data S-in corresponding to the product quality testing parameter 221. Calculating the product quality testing parameter 221 through the above data by the processor 120 include: processing the multiple types of data S-in using a standardization functions S-sta respectively corresponding to multiple types of data S-in (for example, the corresponding standardization functions are S/Smax, P/Pmax, ReH/ReHmin, A/Amin and KV/KVmin, respectively, wherein Smax, Pmax, ReHmin, Amin and KVmin represent the maximum values or the minimum values of corresponding properties in corresponding technical indexes, respectively), to obtain the corresponding standardization data; performing an evaluation process for the corresponding standardization data using evaluation functions (as illustrated in Table 1) respectively corresponding to the multiple types of data S-in to obtain corresponding evaluation processing data S-out; assigning a weight S-per (wherein the sum of weights is 1) to the evaluation processing data corresponding to each type of data, respectively, and calculating a weighted sum of the evaluation processing data S-out corresponding to different types of data to obtain an output parameter $Model_{out}$ as the product quality testing parameter 221; and determining the quality level $Model_{jud}$ of the product based on the output parameter $Model_{out}$.

For example, the output parameter $Model_{out}$ as the product quality testing parameter 221 may be calculated through the following equation:

$$Model_{out} = \sum_{j=1}^{n} W_j x_j,$$

wherein $W_j$ is the evaluation processing data of the j-th type of data, and $x_j$ is a weight value assigned to the evaluation processing data of the j-th type of data.

TABLE 1

Table of Evaluation by Levels for Quality of a Certain Product by Random Inspection of Three Enterprises

|  | S | P | ReH | A | KV | $Model_{out}$ | $Model_{jud}$ | Enterprise Production Line |
|---|---|---|---|---|---|---|---|---|
| S-in | 0.002 | 0.012 | 390 | 34 | 197 |  |  | X steel (single production line) |
|  | 0.008 | 0.02 | 480 | 24 | 85 |  |  | Y steel-refine 1 + roll 1 |
|  | 0.01 | 0.015 | 425 | 30 | 145 |  |  | Y steel-refine 1 + roll 2 |
|  | 0.0015 | 0.0075 | 430 | 38 | 265 |  |  | Y steel-refine 2 + roll 2 |
|  | 0.005 | 0.016 | 437 | 32 | 187 |  |  | Z steel-refine 1 + roll 2 |
|  | 0.0018 | 0.0095 | 395 | 36.5 | 234 |  |  | Z steel-refine 2 + roll 2 |
| S-per | 0.15 | 0.2 | 0.25 | 0.15 | 0.25 |  |  |  |
| S-sta | S/Smax<br>Smax = 0.01 | P/Pmax<br>Pmax = 0.025 | ReH/ReHmin<br>ReHmin = 355 | A/Amin<br>Amin = 20 | KV/KVmin<br>KVmin = 50 |  |  |  |
| S-fun | 1, x ≤ 0.2;<br>1.1-0.5x,<br>0.2 < x ≤1;<br>0, x > 1 | 1, x ≤ 0.32;<br>1.188-0.588x,<br>0.32 < x ≤ 1;<br>0, x > 1 | 0, x < 1;<br>2.667-2.067x,<br>1 ≤ x ≤ 1.15;<br>1, 1.15 < x < 1.25; | 0, x < 1;<br>0.4x + 0.2,<br>1 ≤ x ≤ 2;<br>1, x > 2 | 0, x < 1;<br>0.1x + 0.5,<br>1 ≤ x ≤ 5;<br>1, x > 5 |  |  |  |

TABLE 1-continued

Table of Evaluation by Levels for Quality of a Certain Product by Random Inspection of Three Enterprises

|  | S | P | ReH | A | KV | $Model_{out}$ | $Model_{jud}$ | Enterprise Production Line |
|---|---|---|---|---|---|---|---|---|
| S-out | 1 | 0.906 | 3.5-2x, 1.25 ≤ x < 1.45; 0.6, x ≥ 1.45 0.864 | 0.88 | 0.894 | 0.903 | First level | X steel (single production line) |
|  | 0.7 | 0.718 | 0.797 | 0.68 | 0.67 | 0.717 | Third level | Y steel-refine 1 + roll 1 |
|  | 0.6 | 0.835 | 1 | 0.8 | 0.79 | 0.825 | Second Level | Y steel-refine 1 + roll 2 |
|  | 1 | 1 | 1 | 0.96 | 1 | 0.994 | First Level | Y steel-refine 2 + roll 2 |
|  | 0.85 | 0.818 | 1 | 0.84 | 0.874 | 0.884 | Second Level | Z steel-refine 1 + roll 2 |
|  | 1 | 0.965 | 0.902 | 0.93 | 0.968 | 0.950 | First Level | Z steel-refine 2 + roll 2 |

The results of determination by levels for the samples by random inspection of three enterprises based on the product quality testing parameter 221 are illustrated in Table 1. Wherein random inspection for products may be performed according to production lines of the enterprises. Enterprise X (steel of a first level) is an enterprise with a single production line, and enterprises Y and Z are both enterprises with multiple production lines. In Table 1, indication symbol of the enterprise production line "n enterprise-steelmaking a+rolling b" represents "Melting-casting production line a+Thermoforming production line b" of an iron and steel enterprise n, for example, "Y enterprise-refine 1+roll 1" represents "Melting-casting production line 1+Thermoforming production line 1" of the iron and steel enterprise Y. It may be seen from Table 1 that chemical components occupy 0.35 in the weight assigned to these five types of data, wherein since the control for P element is more difficult than the control for S element and is usually more important than S element in the product quality, the weight of P element is higher than that of S element. Yield strength and impact energy each occupy 0.25 and elongation occupies 0.15 among three mechanical property data. The purpose of standardizing multiple types of data is to make evaluation functions be simplified and uniform as much as possible, and bases of standardization are all index data of technical requirements. It may be further seen from Table 1 that there are three production lines of which the quality levels gain evaluations of the first level among six production lines of the enterprises, and X enterprise, Y enterprise and Z enterprise each have one of them. Meanwhile, there are two production lines gaining evaluations of the second level and the third level, respectively, in the iron and steel enterprise Y. In addition, the product quality testing parameter 221 obtained in Table 1 may be further used for calculating the intrinsic parameter and/or product quality evaluation parameter (see Embodiment 2).

Embodiment 2

Regarding the ship plate product, the technical capability parameter of production line equipment 211, and corresponding melting-casting production line parameter 311 (may also be represented by E–M) and thermoforming production line parameter 312 (may also be represented by E–R) for iron and steel enterprises X, Y and Z are calculated, and the results are seen in Table 2. Since the enterprises Y and Z are both iron and steel companies with multiple production lines, respective production lines are assigned with a weight according to the "procedure succession" principle, and the calculation results are seen in Table 3.

TABLE 2

Table of production line evaluation and assignment of the ship plate product of the enterprise

| | Third Parameter Corresponding to Technical capability parameter of production line equipment | | | | Technical capability parameter of production line equipment | Yield/Ten Thousand Tons |
|---|---|---|---|---|---|---|
| | Thermoforming Production | | Melting-Casting Production | | | |
| Enterprise | Name (Identification) | Line Parameter | Name (Identification) | Line Parameter | | |
| X steel | $(E-R)_X$ | 0.87 | $(E-M)_X$ | 0.83 | 0.85 | 56.0 |
| Y steel | $(E-R)_{Y1}$ | 0.73 | $(E-M)_{Y1}$ | 0.77 | 0.75 | 45.3 |
|  | $(E-R)_{Y2}$ | 0.89 | $(E-M)_{Y1}$ |  | 0.83 | 12.6 |
|  |  |  | $(E-M)_{Y2}$ | 0.97 | 0.93 | 37.8 |
| Z steel | $(E-R)_{Z2}$ | 0.91 | $(E-M)_{Z1}$ | 0.89 | 0.90 | 44.6 |
|  |  |  | $(E-M)_{Z2}$ | 0.81 | 0.86 | 18.2 |

It may be seen from the results of Table 3 that as far as producing the ship-hull plate product, the iron and steel enterprise X only has one melting-casting production line and one thermoforming production line, and thus values of the technical capability parameter of production line equipment 211 calculated by the methods of specific melting-casting+specific thermoforming, a plurality of melting-casting production lines+specific thermoforming production line, the optimum production line equipment technical level and the production line equipment technical average level are the same. For the iron and steel enterprise Y, there are two melting-casting production lines $M_{Y1}$ and $M_{Y2}$ and two thermoforming production lines $R_{y1}$ and $R_{y2}$ for producing a ship plate, and the production lines which can be associated with each other are $R_{Y1}+M_{Y1}$, $R_{Y2}+M_{Y1}$ and $R_{Y2}\pm M_{Y2}$. Wherein since the capability of the melting-casting production line $M_{Y1}$ is comparatively weak (the melting-casting production line parameter is comparatively small), and the capability of the melting-casting production line $M_{Y2}$ is comparatively strong, a weight is assigned to the melting-casting production line parameters corresponding to two melting-casting production lines according to a billet/slab supply ratio and a weighted sum is calculated, in the case where the two melting-casting production lines both provide billet/slab to the production line $R_{Y2}$. For example, a weighted sum of the melting-casting production line parameters of the melting-casting production lines associated with the production line $R_{Y2}$ is: 0.97*0.75+0.77*0.25=0.92. Then the above weighted sum and the thermoforming production line parameter of production line $R_{Y2}$ are fused and further calculated to obtain that the value (i.e., $E(R_{Y2})$) of the technical capability parameter of production line equipment 211 for the production line $R_{Y2}$ is 0.905. Similarly, the value (i.e., $E(R_{Z2})$) of the technical capability parameter of production line equipment 211 for the production line $R_{Z2}$ of the iron and steel enterprise Z, which may be obtained by calculation through the procedure succession algorithm, is 0.888.

In addition, it may be seen from Table 3 that although the optimum production line capability of the iron and steel enterprise Y is the strongest among the three enterprises (the corresponding parameter value is 0.93), the capabilities of the melting-casting production line $M_{Y1}$ and the thermoforming production line $R_{Y1}$ of the iron and steel enterprise Y are comparatively weak (that is, the value of the technical capability parameter of production line equipment $E(R_{Y1}+M_{Y1})$ of the melting-casting production line $M_{Y1}$ and the thermoforming production line $R_{Y1}$ of the iron and steel enterprise Y is relatively small), and the ratio of the yield of the melting-casting production line $MY_1$ and the thermoforming production line $R_{Y1}$ is comparatively high, as a result, technical capability levels of respective production lines are varied, thereby pulling down the enterprise average capability level, and the average level of the enterprise Y is even lower than that of the iron and steel enterprise X. On the contrary, a total level of Z steel is comparatively average, and the yield of the production line $M_{Z1}$ with higher melting-casting capability is far higher than that of the production line $M_{Z2}$, and thus, the enterprise average level thereof is the highest enterprise average level among the three enterprises. The results illustrated in the above Table 3 objectively reflect the equipment technical capability levels of the enterprises in the aspect of producing the ship plate product to a great extend and also further reflects the quality levels of the produced iron and steel products thereof.

TABLE 3

Technical capability parameter of production line equipment of the enterprise ship plate product

| Enterprise | Specific Melting-Casting + Specific Thermoforming | | A Plurality of Melting-Casting Production Lines + Specific Thermoforming | | Optimum Production Line | | Production Line Average Level | |
|---|---|---|---|---|---|---|---|---|
| | Name | Parameter | Name | Parameter | Name | Parameter | Name | Parameter |
| X steel | $E(R_X + M_X)$ | 0.85 | $E(R_X)$ | 0.85 | $E(R_X + M_X)$ | 0.85 | $E_x$ | 0.85 |
| Y steel | $E(R_{Y1} + M_{Y1})$ | 0.75 | $E(R_{Y1})$ | 0.77 | $E(R_{Y2} + M_{Y2})$ | 0.93 | $E_Y$ | 0.832 |
| | $E(R_{Y2} + M_{Y1})$ | 0.83 | $E(R_{Y2})$ | 0.905 | | | | |
| | $E(R_{Y2} + M_{Y2})$ | 0.93 | | | | | | |
| Z steel | $E(R_{Z2} + M_{Z1})$ | 0.90 | $E(R_{Z2})$ | 0.888 | $E(R_{Z2} + M_{Z1})$ | 0.90 | $E_z$ | 0.888 |
| | $E(R_{Z2} + M_{Z2})$ | 0.86 | | | | | | |

In addition, the present disclosure further provides a device for determining a quality level of an iron and steel product which includes a processor configured to perform the above method. However, the exemplary embodiments according to the concept of the present disclosure are not limited thereto, for example, the device for determining a quality level of an iron and steel product according to the exemplary embodiments of the present disclosure may further include an input portion and an output portion. Wherein the input portion may be used for inputting data related to the quality of the iron and steel product into the device for determining the quality level of the iron and steel product, so as to provide the data to the processor. The output portion may be used for outputting a determination result of the quality of the iron and steel product and transmitting the result to a user.

In addition, the method for determining a quality level of the iron and steel product according to the present disclosure may be implemented as a computer program on a computer readable recording medium, and the method is implemented when the computer program is carried out by the processor.

To sum up, a quality level of the iron and steel product may be more sufficiently and truly reflected by comprehensively considering factors direct or indirectly reflecting the quality of the iron and steel product and factors of generating an impact on the quality of the iron and steel product in aspects of production and research and development of the iron and steel product. In addition, the method and device for determining the quality of the iron and steel product according to the concept of the present disclosure may overcome the disadvantages of the current two-value testing system of the "threshold" level and make up deficiencies in the prior art, and can perform continuous numerical evaluation for a quality level of the iron and steel product. Moreover, since the quality level of the product can be determined according to different parameters during the process of determining the quality level of the iron and steel product, factors that need to be considered may be selected in the light of different user demands, which further satisfies diversity demands of different users.

Although the present disclosure has been described with reference to the exemplary embodiments of the present disclosure, it will be understood by those of ordinary skilled in the art that various changes in form and details may be made therein without departing from the spirit and scope of the present disclosure as defined by the following claims and their equivalents. Embodiments should be thought only in a descriptive sense instead of having the purpose of limitation. Thus, the scope of the present disclosure is not defined by detailed embodiments of the present disclosure but defined by the following claims, and all differences within the scope will be explained as being included in the present disclosure.

What is claimed is:

1. A method for determining a quality level of an iron and steel product, the method comprising:
obtaining a plurality of first parameters related to a quality of the iron and steel product;
fusing the plurality of first parameters to obtain a comprehensive quality evaluation parameter; and
determining the quality level of the iron and steel product based on the comprehensive quality evaluation parameter,
wherein:
the method is implemented as a computer program in a device having a computer readable recording medium and a processor, the computer program stored on the computer readable recording medium and carried out by the processor;
the first parameters are obtained through corresponding second parameters, and the second parameters comprise at least one product quality testing parameter and at least one technical capability parameter of production line equipment;
the product quality testing parameter comprises chemical component data and mechanical property data; and
the technical capability parameter of production line equipment comprises a melting-casting production line parameter and a thermoforming production line parameter.

2. The method of claim 1, wherein the technical capability parameter of production line equipment is a parameter reflecting the production line equipment technical capability and obtained through data associated with production equipments and production process parameters of iron and steel products corresponding to respective technological processes during the productive process for producing the iron and steel product.

3. The method of claim 1, wherein the product quality testing parameter is a parameter reflecting the quality of the iron and steel product and obtained based on property testing data of the iron and steel product.

4. The method of claim 1, wherein the technical capability parameter of production line equipment is obtained by:
calculating evaluation processing data corresponding to each type of data among multiple types of data; and fusing all evaluation processing data corresponding to the multiple types of data,
wherein the technical capability of one production line corresponding to one procedure segment among a plurality of procedure segments during the process of producing the iron and steel product, and
wherein the multiple types of data comprise data associated with equipments and process parameters of the one production line.

5. The method of claim 4, wherein the melting-casting production line parameter is a parameter reflecting the technical capability of a melting-casting production line corresponding to a melting-casting procedure segment, the thermoforming production line parameter is a parameter reflecting the technical capability of a thermoforming production line corresponding to a thermoforming procedure segment.

6. The method of claim 5, wherein the obtaining the technical capability parameter of production line equipment comprises fusing the melting-casting production line parameter and the thermoforming production line parameter.

7. The method of claim 6, wherein the fusing the melting-casting production line parameter and the thermoforming production line parameter comprises: assigning a weight to the melting-casting production line parameter corresponding to the corresponding melting-casting production line and to the thermoforming production line parameter corresponding to the corresponding thermoforming production line, respectively, according to a yield of each melting-casting production line and a yield of each thermoforming production line.

8. The method of claim 6, wherein the fusing the melting-casting production line parameter and the thermoforming production line parameter comprises: fusing the melting-casting production line parameter corresponding to each melting-casting production line with the thermoforming production line parameter corresponding to each thermoforming production line which receives billet provided by the each melting-casting production line, respectively, to obtain a plurality of fusion values; and using a maximum fusion value among the plurality of fusion values as the technical capability parameter of production line equipment.

9. The method of claim 1, wherein the method further comprises: determining a quality level of the iron and steel product based on any one specified parameter selected from a group consisting of the product quality testing parameter, the technical capability parameter of production line equipment, the chemical component data, the mechanical property data, the melting-casting production line parameter, and the thermoforming production line parameter.

10. The method of claim 9, wherein the determining the quality level of the iron and steel product based on the any one specified parameter comprises:
when the any one specified parameter is larger than or equal to a first reference value, Ra, determining the quality level of the iron and steel product to be a first level; when the any one specified parameter is larger than or equal to a second reference value, Rb, and is less than Ra, determining the quality level of the iron and steel product to be a second level; when the any one specified parameter is less than Rb and is larger than or equal to a third reference value, Rc, determining the quality level of the iron and steel product to be a third level; and when the any one specified parameter is less than Rc, determining the quality level of the iron and steel product to be a fourth level, where Ra>Rb>Rc, and
wherein the quality of the iron and steel product of the first level is better than the quality of the iron and steel product of the second level, the quality of the iron and steel product of the second level is better than the quality of the iron and steel product of the third level, and the quality of the iron and steel product of the third level is better than the quality of the iron and steel product of the fourth level.

11. The method of claim 10, wherein Ra is set to 0.9, Rb is set to 0.75, and Rc is set to 0.60.

12. The method of claim 9, wherein when quality levels of more than or equal to a specified number of a plurality of iron and steel products are determined, the any one specified parameter corresponding to each iron and steel product is obtained, respectively, wherein the determining quality levels of the plurality of iron and steel products based on the any one specified parameter comprises: ranking specified parameters larger than or equal to Rd included in the any one specified parameter of the plurality of iron and steel products; when a ranking proportion of the any one specified parameter of any one iron and steel product of the plurality of iron and steel products is less than or equal to a first reference ratio, aa %, determining a quality level of the any one iron and steel product to be a first level; when the ranking proportion of the any one specified parameter of the any one iron and steel product is less than or equal to a second reference ratio, bb %, and is larger than aa %, determining the quality level of the any one iron and steel product to be a second level; and when the ranking proportion of the any one specified parameter of the any one iron and steel product is larger than or equal to bb % or the any one specified parameter of any one iron and steel product is less than a first reference value, Rd, determining the quality level of the any one iron and steel product to be a third level, where bb %>aa %, wherein the ranking proportion of the any one specified parameter of the any one iron and steel product indicates: (a ranking number of the any one specified parameter of the any one iron and steel product/a total number of the any one specified index parameter involved in ranking and included in the any one specified parameter of the plurality of iron and steel products)×100%, and wherein the quality of the any one iron and steel product of the first level is better than the quality of the any one iron and steel product of the second level, and the quality of the any one iron and steel product of the second level is better than the quality of the any one iron and steel product of the third level.

13. The method of claim 12, wherein aa % is set to 15%, bb % is set to 70%, and Rd is set to 0.60.

* * * * *